US00PP26463P2

(12) United States Plant Patent
Misato

(10) Patent No.: US PP26,463 P2
(45) Date of Patent: Mar. 8, 2016

(54) ***VERBENA* PLANT NAMED 'SUNTAPIMABAI'**

(50) Latin Name: *Verbena×hybrida*
Varietal Denomination: Suntapimabai

(71) Applicant: Tomoya Misato, Shiga (JP)

(72) Inventor: Tomoya Misato, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 240 days.

(21) Appl. No.: 13/998,605

(22) Filed: Nov. 15, 2013

(51) Int. Cl.
*A01H 5/02* (2006.01)

(52) U.S. Cl.
USPC ..... Plt./308

(58) Field of Classification Search
USPC ..... Plt./308
See application file for complete search history.

*Primary Examiner* — Anne Grunberg
(74) *Attorney, Agent, or Firm* — C. A. Whealy

(57) ABSTRACT

A new and distinct cultivar of *Verbena* plant named 'Suntapimabai', characterized by its semi-upright and mounding plant habit; vigorous growth habit; freely branching habit; early and freely flowering habit; and intense purple violet-colored flowers that are held above and beyond the foliar plane.

1 Drawing Sheet

Botanical designation: *Verbena×hybrida.*
Cultivar denomination: 'SUNTAPIMABAI'.

BACKGROUND OF THE INVENTION

The present invention relates to a new and distinct cultivar of *Verbena* plant, botanically known as *Verbena×hybrida* and hereinafter referred to by the name 'Suntapimabai'.

The new *Verbena* plant is a product of a planned breeding program conducted by the Inventor in Higashiomi, Shiga, Japan. The objective of the breeding program is to create new freely branching *Verbena* plants with semi-upright and mounding plant habit and attractive flowers.

The new *Verbena* plant originated from a cross-pollination made by the Inventor in April, 2010 in Higashiomi, Shiga, Japan of a proprietary selection of *Verbena×hybrida* identified as code number SUNV46, not patented, as the female, or seed, parent with a proprietary selection of *Verbena×hybrida* identified as code number SUNV19, not patented, as the male, or pollen, parent. The new *Verbena* plant was discovered and selected by the Inventor as a single flowering plant from within the progeny of the stated cross-pollination in a controlled greenhouse environment in Higashiomi, Shiga, Japan in October, 2010.

Asexual reproduction of the new *Verbena* plant by cuttings in a controlled greenhouse environment in Higashiomi, Shiga, Japan since October, 2010 has shown that the unique features of this new *Verbena* plant are stable and reproduced true to type in successive generations.

SUMMARY OF THE INVENTION

Plants of the new *Verbena* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Suntapimabai'. These characteristics in combination distinguish 'Suntapimabai' as a new and distinct *Verbena* plant:

1. Semi-upright and mounding plant habit.
2. Vigorous growth habit.
3. Freely branching habit.
4. Early and freely flowering habit.
5. Intense purple violet-colored flowers that are held above and beyond the foliar plane.

Plants of the new *Verbena* can be compared to plants of the female and male parent selections. Plants of the new *Verbena* differ primarily from plants of the female and male parent selections in plant size as plants of the new *Verbena* are taller than plants of the female and male parent selections. In addition, plants of the new *Verbena* and the female and male parent selections differ in flower color as plants of the female parent selection have light pink-colored flowers and plants of the male parent selection have deep violet-colored flowers.

Plants of the new *Verbena* can be compared to plants of the *Verbena×hybrida* 'Sunmaref TP-V', disclosed in U.S. Plant Pat. No. 9,411. In side-by-side comparisons conducted in Higashiomi, Shiga, Japan, plants of the new *Verbena* differed primarily from plants of 'Sunmaref TP-V' in the following characteristics:

1. Plants of the new *Verbena* were more upright and mounding than and not as trailing as plants of 'Sunmaref TP-V'.
2. Plants of the new *Verbena* were taller than and not as broad as plants of 'Sunmaref TP-V'.
3. Plants of the new *Verbena* and 'Sunmaref TP-V' differed in flower color as plants of 'Sunmaref TP-V' had vivid purple-colored flowers.

BRIEF DESCRIPTION OF THE PHOTOGRAPHS

The accompanying colored photographs illustrate the overall appearance of the new *Verbena* plant showing the colors as true as it is reasonably possible to obtain in colored reproductions of this type. Colors in the photographs may differ slightly from the color values cited in the detailed botanical description which accurately describe the colors of the new *Verbena* plant.

The photograph at the top of the sheet comprises a side perspective view of a typical flowering plant of 'Suntapimabai' grown in a container.

The photograph at the bottom of the sheet is a close-up view of a typical flowering plant of 'Suntapimabai'.

DETAILED BOTANICAL DESCRIPTION

The aforementioned photographs and following observations and measurements describe plants grown during the summer in 15-cm containers in an outdoor nursery in Higashiomi, Shiga, Japan and under cultural practices typical of commercial *Verbena* production. During the production of the plants, day temperatures averaged 23° C. and night temperatures averaged 13° C. Plants were four months old when the photographs and description were taken. In the following description, color references are made to The Royal Horticultural Society Colour Chart, 2007 Edition, except where general terms of ordinary dictionary significance are used.

Botanical classification: *Verbena×hybrida* 'Suntapimabai'.

Parentage:

*Female, or seed, parent*.—Proprietary selection of *Verbena×hybrida* identified as code number SUNV46, not patented.

*Male, or pollen, parent*.—Proprietary selection of *Verbena×hybrida* identified as code number SUNV19, not patented.

Propagation:

*Type*.—By cuttings.

*Time to initiate roots, summer and winter*.—About 10 to 14 days at temperatures about 20° C. to 25° C.

*Time to produce a rooted young plant, summer and winter*.—About four weeks at temperatures about 20° C. to 25° C.

*Root description*.—Fibrous; white in color.

*Rooting habit*.—Freely branching.

Plant description:

*Plant and growth habit*.—Semi-upright and mounding plant habit; freely branching habit with numerous lateral branches developing per plant, pinching enhances lateral branch development; vigorous growth habit.

*Plant height*.—About 22.4 cm.

*Plant diameter*.—About 63.9 cm.

Lateral branch description:

*Length*.—About 19.5 cm.

*Diameter*.—About 2 mm.

*Internode length*.—About 3.22 cm.

*Strength*.—Strong; flexible.

*Texture*.—Pubescent.

*Color*.—Close to 138C; distally tinged with close to N81A.

Leaf description:

*Arrangement*.—Opposite, simple.

*Length*.—About 3 cm.

*Width*.—About 2.22 cm.

*Shape*.—Broadly angular to ovate; pinnately cleft with deep incisions.

*Apex*.—Acute.

*Base*.—Truncate.

*Margin*.—Pinnately cleft with deep incisions.

*Texture, upper and lower surfaces*.—Pubescent, coarse.

*Venation pattern*.—Pinnate; reticulate.

*Color*.—Developing leaves, upper surface: Close to 137B. Developing leaves, lower surface: Close to 137D. Fully expanded leaves, upper surface: Close to 137A; venation, close to 137A. Fully expanded leaves, lower surface: Close to 137D; venation, close to 138C.

*Petioles*.—Length: About 7.6 mm. Diameter: About 2.2 mm. Texture, upper and lower surfaces: Pubescent. Color, upper and lower surfaces: Close to 145A.

Flower description:

*Flower arrangement and habit*.—Salverform flowers arranged in hemispherical terminal racemes; flowers face mostly upright and outwardly; flowers sessile; freely flowering habit with about ten flowers per inflorescence and about 112 inflorescences developing per plant.

*Natural flowering season*.—Plants flower continuously from spring to late autumn in Japan; plants begin flowering about four weeks after planting.

*Flower longevity*.—Flowers last about one week on the plant; flowers not persistent.

*Fragrance*.—None detected.

*Inflorescence height*.—About 2.25 cm.

*Inflorescence diameter*.—About 3.92 cm.

*Flowers*.—Appearance: Flared trumpet, corolla fused, five-parted. Diameter: About 1.53 cm. Depth (height): About 1.75 cm. Tube length: About 1.4 cm. Tube diameter, mid-section: About 1.3 mm.

*Flower buds*.—Length: About 1.06 cm. Diameter: About 2.8 mm. Shape: Clavate. Color: Close to N89B.

*Corolla*.—Arrangement: Single whorl of five fused petals. Petal length: About 7.1 mm. Petal width: About 6.3 mm. Petal lobe shape: Cordate. Petal lobe apex: Cordate. Petal lobe margin: Entire; slightly undulate. Petal texture, upper and lower surfaces: Smooth, glabrous. Color: Petal, when opening, upper surface: Lighter than 83A. Petal, when opening, lower surface: Close to 83B. Petal, fully opened, upper surface: Close to N81A; color becoming lighter than N81A with development. Petal, fully opened, lower surface: Close to N81B. Throat: Close to 193C; distally, close to 77B. Tube: Close to 193C; distally, close to 77C.

*Calyx*.—Arrangement: Narrow tubular calyx comprised of five fused sepals. Sepal length: About 1.2 mm. Sepal width: About 1 mm. Sepal shape: Triangular. Sepal apex: Acute. Sepal margin: Entire. Sepal texture, upper and lower surfaces: Pubescent. Sepal color: When developing and fully developed, upper surface: Close to 144A; towards the apex, close to 64A. When developing and fully developed, lower surface: Close to 144B.

*Peduncles*.—Length: About 3.1 cm. Diameter: About 1.5 mm. Strength: Strong; flexible. Texture: Pubescent. Color: Close to 137B.

*Reproductive organs*.—Stamens: Quantity and arrangement: Four per flower, adnate to corolla tube. Anther shape: Ellipsoidal. Anther size: About 0.7 mm by 1 mm. Anther color: Close to 149B. Pollen amount: None observed. Pistils: Quantity: One per flower. Pistil length: About 1.1 cm. Stigma shape: Bi-parted. Stigma color: Close to 141A. Style color: Close to 141D. Ovary color: Close to 141A. Fruits and seeds: Fruit and seed development have not been observed on plants of the new *Verbena*.

Temperature tolerance: Plants of the new *Verbena* have been observed to tolerate temperatures from about 0° C. to about 35° C.

Pathogen & pest resistance: Plants of the new *Verbena* have not been observed to be resistant to pathogens and pests common to *Verbena* plants.

It is claimed:

1. A new and distinct *Verbena* plant named 'Suntapimabai' as illustrated and described.

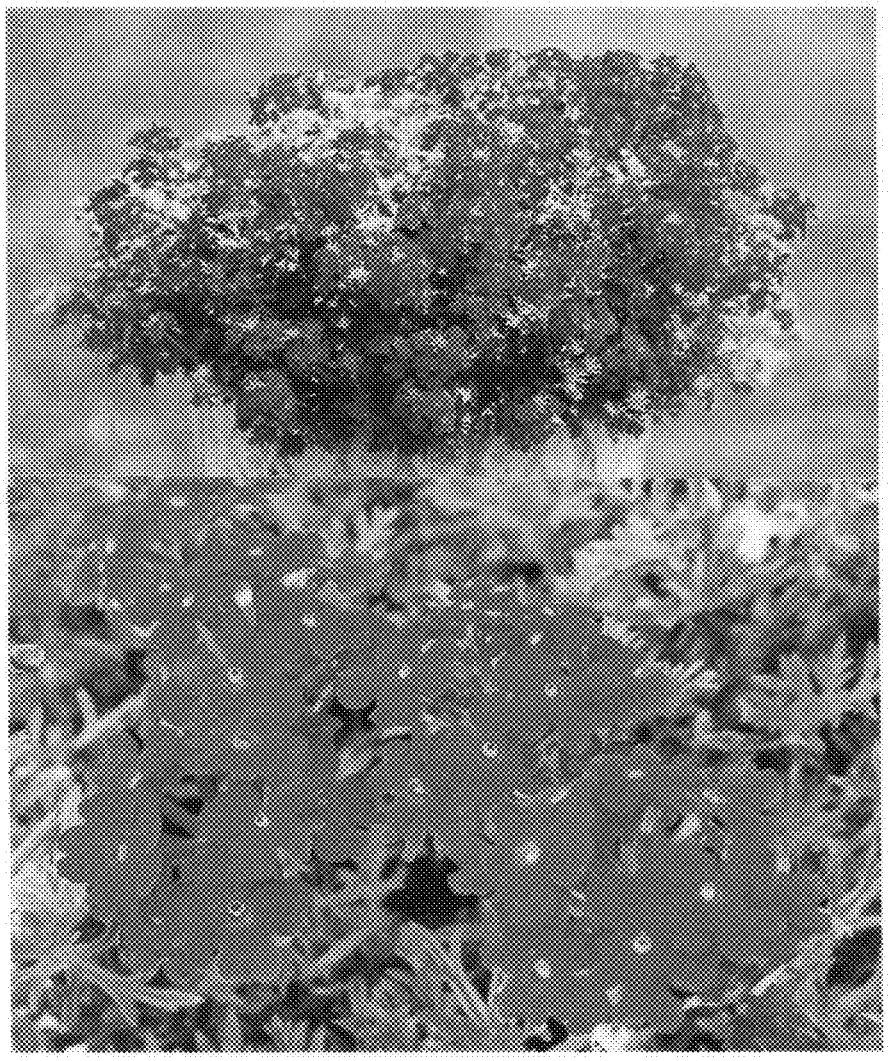

* * * * *